(12) United States Patent
Zhao

(10) Patent No.: US 10,877,117 B2
(45) Date of Patent: Dec. 29, 2020

(54) GRADIENT AMPLIFIER

(71) Applicant: Shanghai Neusoft Medical Technology Co., Ltd., Shanghai (CN)

(72) Inventor: Hongju Zhao, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 556 days.

(21) Appl. No.: 15/682,861

(22) Filed: Aug. 22, 2017

(65) Prior Publication Data

US 2018/0059197 A1 Mar. 1, 2018

(30) Foreign Application Priority Data

Aug. 31, 2016 (CN) .......................... 2016 1 0784582

(51) Int. Cl.
*G01R 33/385* (2006.01)
*A61B 5/055* (2006.01)
*G01R 33/36* (2006.01)

(52) U.S. Cl.
CPC .......... *G01R 33/3852* (2013.01); *A61B 5/055* (2013.01); *G01R 33/36* (2013.01)

(58) Field of Classification Search
CPC ...... G01R 33/36; G01R 33/3852; A61B 5/055
See application file for complete search history.

(56) References Cited

U.S. PATENT DOCUMENTS

2014/0077812 A1* 3/2014 Sabate ............... G01R 33/3852
324/319
2018/0231623 A1* 8/2018 Lin ..................... G01R 33/3852
2019/0150783 A1* 5/2019 Xue ..................... G01R 33/341

FOREIGN PATENT DOCUMENTS

| CN | 201123165 Y | 9/2008 |
|---|---|---|
| CN | 201138785 Y | 10/2008 |
| CN | 101651408 A | 2/2010 |
| CN | 201656765 U | 11/2010 |
| CN | 203275625 U | 11/2013 |
| CN | 104142483 A | 11/2014 |

(Continued)

OTHER PUBLICATIONS

English translation of CN104950273 provided by Google Translate. (Year: 2020).*

(Continued)

*Primary Examiner* — Rishi R Patel

(74) *Attorney, Agent, or Firm* — Fish & Richardson P.C.

(57) ABSTRACT

Methods, devices and systems for providing a high-precision and fast changing driving current for a gradient coil to generate a gradient magnetic field to acquire a high-quality image in an MRI device are provided. An example gradient amplifier includes a controller, a power amplifying circuit and a filtering circuit. The controller is configured to output pulse signals. The power amplifying circuit includes a first H bridge circuit and a second H bridge circuit and is configured to perform power conversion on an input power supply according to the pulse signals to output a driving current to a gradient coil. The filtering circuit is configured to filter the driving current output by the power amplifying circuit. A phase difference between the pulse signals output by the controller to drive switching tubes on a same position in the first H bridge circuit and the second H bridge circuit is a particular degree.

12 Claims, 4 Drawing Sheets

(56) References Cited

FOREIGN PATENT DOCUMENTS

| | | |
|---|---|---|
| CN | 104950273 A | 9/2015 |
| CN | 105785295 A | 7/2016 |
| WO | 2016050800 A2 | 4/2016 |

OTHER PUBLICATIONS

State Intellectual Property Office of the People's Republic of China, Office Action and Search Report Issued in Application No. 201610784582.6, dated Jul. 26, 2018, 8 pages, and an English translation of the Office Action.

Hu Hong-bing, Wang Yan-long, Zhao Hong-ju,A Control Technology for Gradient Amplifier Based on Multi-Frequency Shift, Chinese Journal of Magnetic Resonance, vol. 32 No. 1, Mar. 2015, 9 pages.

Watanabe S et al: "Development of digital optimum predictive control implementation for gradient magnetic field current controller in MRI system," Power Conversion Conference, 2002.PCC-OSAKA 2002. Proceedings of the Osaka, Japan Apr. 2-5, 2002, Piscataway, NJ, USA, IEEE, US. vol.3,Apr. 2, 2002 (Apr. 2, 2002), pp. 999-1004, XP010590294, DOI:10.1109/PCC.2002.998108 ISBN:978-0-7803-7156-9.

Siqi Li et al : "Stacked high/low voltage level H-bridge circuit for gradient amplifier of MRI system," Electrical Machines and Systems, 2008. ICEMS 2008. International Conference On, IEEE, Piscataway, NJ, USA, Oct. 17, 2008 (Oct. 17, 2008), pp. 2154-2158, XP031416104, ISBN: 978-1-4244-3826-6.

Caris M La et al: "Generalized harmonic elimination method for interleaved power amplifiers," IECON 2012—38th Annual Conference on IEEE Industrial Electronics Society, IEEE, Oct. 25, 2012 (Oct. 25, 2012), pp. 4979-4984, XP032281325, DOI: HI.1HI9/IECON.2012.6388985 ISBN: 978-1-4673-2419-9.

European Patent Office: European Search Report mailed in corresponding European Patent Application No. 17187628.7 dated May 11, 2018 (9 pages).

State Intellectual Property Office of the People's Republic of China, Office Action and Search Report Issued in Chinese Application No. 201610784582.6, dated May 13, 2019, 24 pages (Submitted with Machine Translation).

State Intellectual Property Office of the People's Republic of China, Office Action and Search Report Issued in Chinese Application No. 201610784582.6, dated Nov. 14, 2019, 25 pages. (Submitted with Machine Translation).

European Patent Office, Office Action Issued in European Application No. 17187628.7, dated Nov. 28, 2019, Germany, 6 pages.

He Hong et al., "A switching power supply EMI filter" Switching Power Supply Electromagnetic Compatibility, Dec. 31, 2008, 2 pages.(Submitted with Partial Translation).

State Intellectual Property Office of the People's Republic of China; Decision of Rejection Issued in couterpart Chines Patent Application No. 201607845852.6, dated Jul. 1, 2020, 12 pages (Submitted with English-Language Machine Translation).

* cited by examiner

GRADIENT AMPLIFIER

CROSS REFERENCE TO RELATED APPLICATIONS

The present disclosure claims priority to Chinese Patent Application No. 201610784582.6 filed on Aug. 31, 2016, the entire content of which is incorporated herein by reference.

TECHNICAL FIELD

The present disclosure relates to a gradient amplifier, which can be applied to a magnetic resonance imaging device.

BACKGROUND

Magnetic resonance imaging (MRI) has become an important means of clinical imaging examination. As an important part of an MRI device, a gradient amplifier can provide a driving current for a gradient coil to generate a gradient magnetic field for imaging. To acquire a high-quality image, it is desirable for the gradient amplifier to provide a high-precision and fast changing driving current for the coil, and an output waveform of the driving current can have a trapezoidal shape.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices and systems for providing a high-precision and fast changing driving current for a gradient coil to generate a gradient magnetic field to acquire a high-quality image.

One aspect of the present disclosure features a gradient amplifier including: a controller configured to output pulse signals, a power amplifying circuit configured to perform power conversion on an input power supply according to the pulse signals to output a driving current, and a filtering circuit configured to filter the driving current output by the power amplifying circuit. The power amplifying circuit includes: a first H bridge circuit having switching tubes; and a second H bridge circuit coupled in parallel with the first H bridge circuit and having an essentially identical structure as the first H bridge circuit, and a phase difference between the pulse signals output by the controller to drive switching tubes on a same position in the first H bridge circuit and the second H bridge circuit is a particular degree. The filter circuit includes at least one of: a differential-mode inductor set configured to filter out differential-mode noise in the driving current, a common-mode inductor set configured to filter out common-mode noise in the driving current, or a filtering capacitor.

In some implementations, the differential-mode inductor set includes a first differential-mode inductor set including a first differential-mode inductor and a second differential-mode inductor, the first differential-mode inductor being coupled with the second differential-mode inductor. The common-mode inductor set includes a first common-mode inductor set including a first common-mode inductor and a second common-mode inductor, the first common-mode inductor being coupled with the second common-mode inductor. A first output terminal of the first H bridge circuit is coupled with a second output terminal of the first H bridge circuit sequentially through the first differential-mode inductor, the first common-mode inductor, two output terminals of the filtering circuit, the second common-mode inductor and the second differential-mode inductor.

In some examples, a first terminal of the first differential-mode inductor is coupled with the first output terminal of the first H bridge circuit, a second terminal of the first differential-mode inductor is coupled with a first terminal of the first common-mode inductor, a second terminal of the first common-mode inductor is coupled with a second terminal of the second common-mode inductor, a first terminal of the second common-mode inductor is coupled with a first terminal of the second differential-mode inductor, and a second terminal of the second differential-mode inductor is coupled with the second output terminal of the first H bridge circuit.

In some implementations, the differential-mode inductor set includes a second differential-mode inductor set including a third differential-mode inductor and a fourth differential-mode inductor, the third differential-mode inductor being coupled with the fourth differential-mode inductor. The common-mode inductor set includes a second common-mode inductor set including a third common-mode inductor and a fourth common-mode inductor, the third common-mode inductor being coupled with the fourth common-mode inductor. A first output terminal of the second H bridge circuit is coupled with a second output terminal of the second H bridge circuit sequentially through the third differential-mode inductor, the third common-mode inductor, the two output terminals of the filtering circuit, the fourth common-mode inductor and the fourth differential-mode inductor.

In some examples, a first terminal of the third differential-mode inductor is coupled with the first output terminal of the second H bridge circuit, a second terminal of the third differential-mode inductor is coupled with a first terminal of the third common-mode inductor, a second terminal of the third common-mode inductor is coupled with a second terminal of the fourth common-mode inductor, a first terminal of the fourth common-mode inductor is coupled with a first terminal of the fourth differential-mode inductor, and a second terminal of the fourth differential-mode inductor is coupled with the second output terminal of the second H bridge circuit.

The filtering capacitor can include a first filtering capacitor and a second filtering capacitor. The second filtering capacitor and the first filtering capacitor can be coupled in series between two output terminals of the filtering circuit, and a common terminal of the first filtering capacitor and the second filtering capacitor can be grounded.

In some implementations, the first H bridge circuit comprises a first switching tube, a second switching tube, a third switching tube and a fourth switching tube. The first switching tube and the second switching tube are coupled in series between a positive and a negative of the input power supply, and a common terminal of the first switching tube and the second switching tube serves as the first output terminal of the first H bridge circuit. The third switching tube and the fourth switching tube are coupled in series between the positive and the negative of the input power supply, and a common terminal of the third switching tube and the fourth switching tube serves as the second output terminal of the first H bridge circuit. The pulse signals for driving the first switching tube and the second switching tube are of opposite phases, the pulse signals for driving the third switching tube and the fourth switching tube are of opposite phases, and a phase difference between the pulse signals for driving the first switching tube and the fourth switching tube is 180 degrees.

The switching tubes in the first H bridge circuit and the second H bridge circuit can include at least one of a Negative Metal Oxide Semiconductor (NMOS) tube, an Insulated Gate Bipolar Transistor (IGBT) tube, or a Metal Oxide Semiconductor Field Effect Transistor (MOSFET) tube.

Another aspect of the present disclosure features a magnetic resonance imaging (MRI) device, comprising: a coil configured to generate a magnetic field and a gradient amplifier configured to provide a driving current for the coil. The gradient amplifier includes: a controller configured to output pulse signals; a power amplifying circuit configured to perform power conversion on an input power supply according to the pulse signals to output the driving current, and a filtering circuit configured to filter the driving current output by the power amplifying circuit. The power amplifying circuit includes: a first H bridge circuit including switching tubes and a second H bridge circuit coupled in parallel with the first H bridge circuit and having an essentially identical structure as the first H bridge circuit. A phase difference between the pulse signals output by the controller to drive the switching tubes on a same position in the first H bridge circuit and the second H bridge circuit is a particular degree. The filtering circuit includes at least one of: a differential-mode inductor set configured to filter out differential-mode noise in the driving current; a common-mode inductor set configured to filter out common-mode noise in the driving current; or a filtering capacitor.

In some implementations, the differential-mode inductor set includes a first differential-mode inductor set including a first differential-mode inductor and a second differential-mode inductor, the first differential-mode inductor being coupled with the second differential-mode inductor. The common-mode inductor set comprises a first common-mode inductor set including a first common-mode inductor and a second common-mode inductor, the first common-mode inductor being coupled with the second common-mode inductor. A first output terminal of the first H bridge circuit is coupled with a second output terminal of the first H bridge circuit sequentially through the first differential-mode inductor, the first common-mode inductor, two output terminals of the filtering circuit, the second common-mode inductor and the second differential-mode inductor.

In some examples, a first terminal of the first differential-mode inductor is coupled with the first output terminal of the first H bridge circuit, a second terminal of the first differential-mode inductor is coupled with a first terminal of the first common-mode inductor, a second terminal of the first common-mode inductor is coupled with a second terminal of the second common-mode inductor through the coil, a first terminal of the second common-mode inductor is coupled with a first terminal of the second differential-mode inductor, and a second terminal of the second differential-mode inductor is coupled with the second output terminal of the first H bridge circuit.

In some implementations, the differential-mode inductor set includes a second differential-mode inductor set including a third differential-mode inductor and a fourth differential-mode inductor, the third differential-mode inductor being coupled with the fourth differential-mode inductor. The common-mode inductor set comprises a second common-mode inductor set including a third common-mode inductor and a fourth common-mode inductor, the third common-mode inductor being coupled with the fourth common-mode inductor. A first output terminal of the second H bridge circuit is coupled with a second output terminal of the second H bridge circuit sequentially through the third differential-mode inductor, the third common-mode inductor, two output terminals of the filtering circuit, the fourth common-mode inductor and the fourth differential-mode inductor.

In some examples, a first terminal of the third differential-mode inductor is coupled with the first output terminal of the second H bridge circuit, a second terminal of the third differential-mode inductor is coupled with a first terminal of the third common-mode inductor, a second terminal of the third common-mode inductor is coupled with a second terminal of the fourth common-mode inductor through the coil, a first terminal of the fourth common-mode inductor is coupled with a first terminal of the fourth differential-mode inductor, and a second terminal of the fourth differential-mode inductor is coupled with the second output terminal of the second H bridge circuit.

The filtering capacitor can include a first filtering capacitor and a second filtering capacitor. The second filtering capacitor and the first filtering capacitor can be coupled in series between two output terminals of the filtering circuit, and a common terminal of the first filtering capacitor and the second filtering capacitor can be grounded.

In some implementations, the first H bridge circuit includes a first switching tube, a second switching tube, a third switching tube and a fourth switching tube. The first switching tube and the second switching tube are coupled in series between an positive and a negative of the input power supply, and a common terminal of the first switching tube and the second switching tube serves as the first output terminal of the first H bridge circuit. The third switching tube and the fourth switching tube are coupled in series between the positive and the negative of the input power supply, and a common terminal of the third switching tube and the fourth switching tube serves as the second output terminal of the first H bridge circuit. The pulse signals for driving the first switching tube and the second switching tube are of opposite phases, the pulse signals for driving the third switching tube and the fourth switching tube are of opposite phases, and a phase difference between the pulse signals for driving the first switching tube and the fourth switching tube is 180 degrees.

The switching tubes of the first H bridge circuit and the second bridge circuit can include at least one of a Negative Metal Oxide Semiconductor (NMOS) tube, an Insulated Gate Bipolar Transistor (IGBT) tube, or a Metal Oxide Semiconductor Field Effect Transistor (MOSFET) tube.

A further aspect of the present disclosure features a method of controlling a gradient amplifier by a controller, including: outputting a first group of pulse signals to respectively control each of switching tubes in a first H bridge circuit and outputting a second group of pulse signals to respectively control each of switching tubes in a second H bridge circuit. The first H bridge circuit and the second H bridge circuit have an essentially identical structure and are coupled in parallel to form a power amplifying circuit, and the pulse signals for driving the switching tubes on a same position in the first H bridge circuit and the second H bridge circuit have a particular phase difference.

In some implementations, the first H bridge circuit comprises first and second output terminals coupled to two respective ends of a coil and is configured to output first and second output signals at the first and second output terminals, respectively. Outputting a first group of pulse signals includes outputting the first group of pulses signals to control the first and second output signals to form a first driving current flowing through the coil. The second H bridge circuit comprises third and fourth output terminals coupled to the two respective ends of the coil and is configured to output third and fourth output signals at the third and fourth output terminals, respectively. Outputting a second group of pulse signals includes outputting the second group of pulses signals to control the third and fourth output signals to form a second driving current flowing through the coil.

The particular phase difference can be configured such that a total driving current on the coil that is based on the first driving current and the second driving current has a higher frequency than one of the first driving current and the second driving current. In some examples, the particular phase difference is 90 degrees, and a frequency of the total driving current is doubled compared to a frequency of the one of the first driving current and the second driving current.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
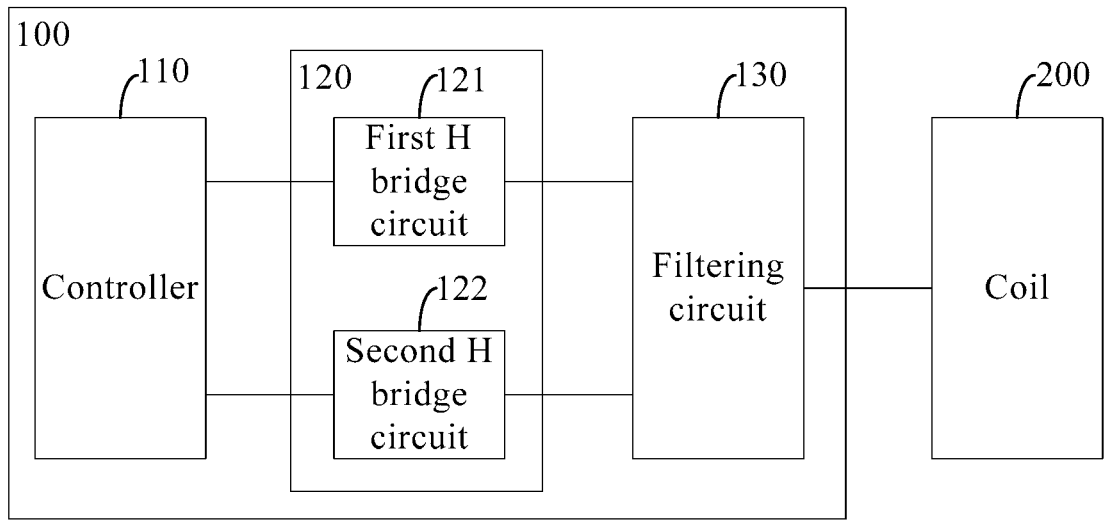
FIG. 1 illustrates a schematic diagram of a gradient amplifier according to an example of the present disclosure.

FIG. 1 illustrates a schematic diagram of a gradient amplifier according to an example of the present disclosure.

The gradient amplifier can be applied to an MRI device. In some implementations, the gradient amplifier 100 includes a controller 110, a power amplifying circuit 120 and a filtering circuit 130.

The controller 110 can be configured to output a pulse signal to the power amplifying circuit 120, so as to control turn-on and turn-off of switching tubes in the power amplifying circuit 120. It is noted that the controller 100 may directly output a pulse signal through a microprocessor or a chip such as a digital signal process (DSP). For example, the controller 110 may automatically regulate and optimize corresponding proportion, integration and differentiation (PID) parameters according to one or more characteristics of a load, so as to output a pulse width modulation (PWM) control signal.

The power amplifying circuit 120 can be configured to perform power conversion on an input power supply and then provide a driving current for the filtering circuit 130. In some implementations, the power amplifying circuit 120 includes a first H bridge circuit 121 and a second H bridge circuit 122 in parallel. The first H bridge circuit 121 and the second H bridge circuit 122 can have an essentially or substantially identical structure. In a particular example, the first H bridge circuit 121 and the second H bridge circuit 122 have the same structure.

A phase difference between pulse signals for driving switching tubes on a same position in the first H bridge circuit 121 and the second H bridge circuit 122 may be 90 degrees. The phase difference of 90 degrees between the pulse signals for driving the switching tubes on the same position in the two H bridge circuits 121 and 122 may double a frequency of the driving current loaded on a gradient coil 200. The coil 200 may be a receiving coil or a transmitting coil.

The filtering circuit 130 can be configured to filter the driving current outputted from the power amplifying circuit 120 and then output the driving current to the coil 200. In some cases, as each of the switching tubes in the double H bridge circuits 121 and 122 works in a hard switching mode, a high-frequency electromagnetic interference signal may exist in the driving currents output by the first H bridge circuit 121 and the second H bridge circuit 122. The hard switching mode can be obtained by conducting and interrupting a power flow so as to turn on and off a switching tube. In the hard switch mode, there may be an abrupt changed switching process, which may cause a relatively high electromagnetic interference signal.

In some implementations, the filtering circuit 130 includes a differential-mode inductor set, a common-mode inductor set, and/or a filtering capacitor. The differential-mode inductor set can be configured to filter out differential-mode noise in the driving current. The common-mode inductor set can be configured to filter out common-mode noise in the driving current. That is, the differential-mode inductor set and the common-mode inductor set in the filtering circuit can be used to filter out both the differential-mode noise and the common-mode noise included in the driving current. The filtering capacitor in the filtering circuit 130 can be further configured to filter out the common-mode noise in the driving current and reduce ripple current in an output current. Therefore, after the filtering circuit 130 filters out the differential-mode noise and the common-mode noise, the driving current provided for the coil 200 may be relatively accurate. In this way, an imaging effect or quality of the MRI device can be guaranteed.

In some examples, a phase difference between the pulse signals output by the controller 100 to drive the switching tubes on the same position in the two H bridge circuits 121 and 122 can be a particular degree, such as 45 degrees, 90 degrees, 135 degrees and so on. It is noted that the phase difference 90 degrees can be taken as an example in the present disclosure. In this way, the frequency of the driving current finally loaded on the coil 200 can be doubled so that a high-frequency current signal can be provided for the coil 200.

Figure 2:
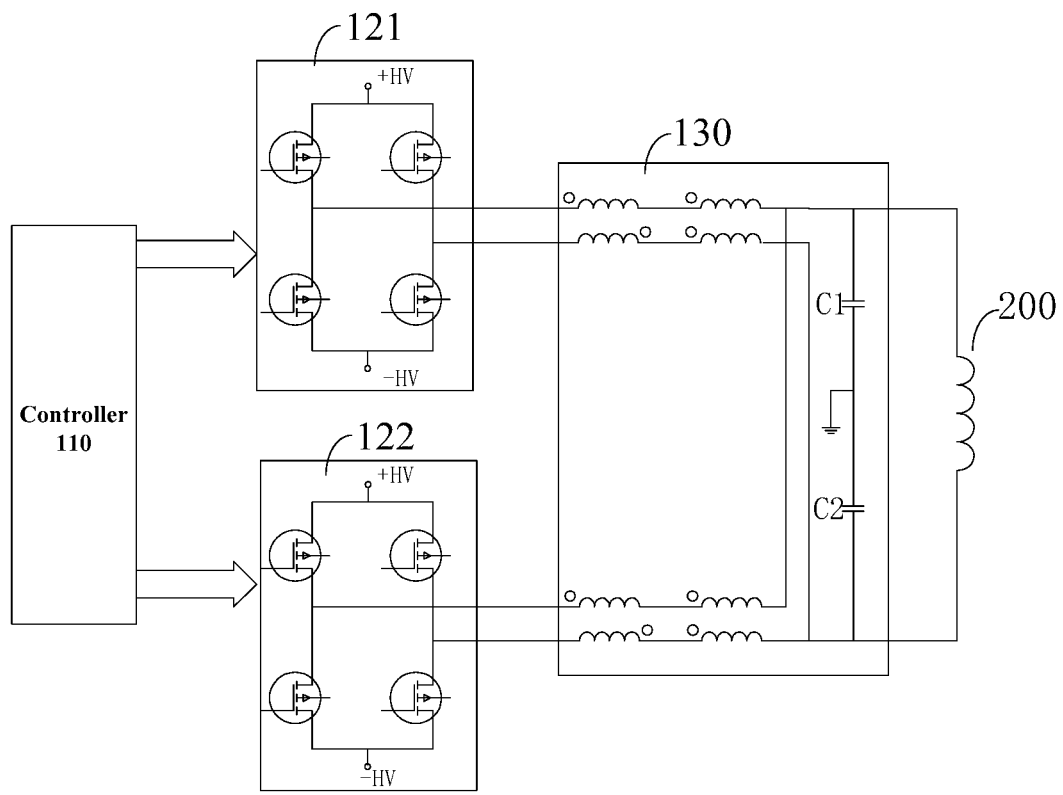
FIG. 2 illustrates a schematic diagram of a circuit of a gradient amplifier according to an example of the present disclosure.
Figure 3:
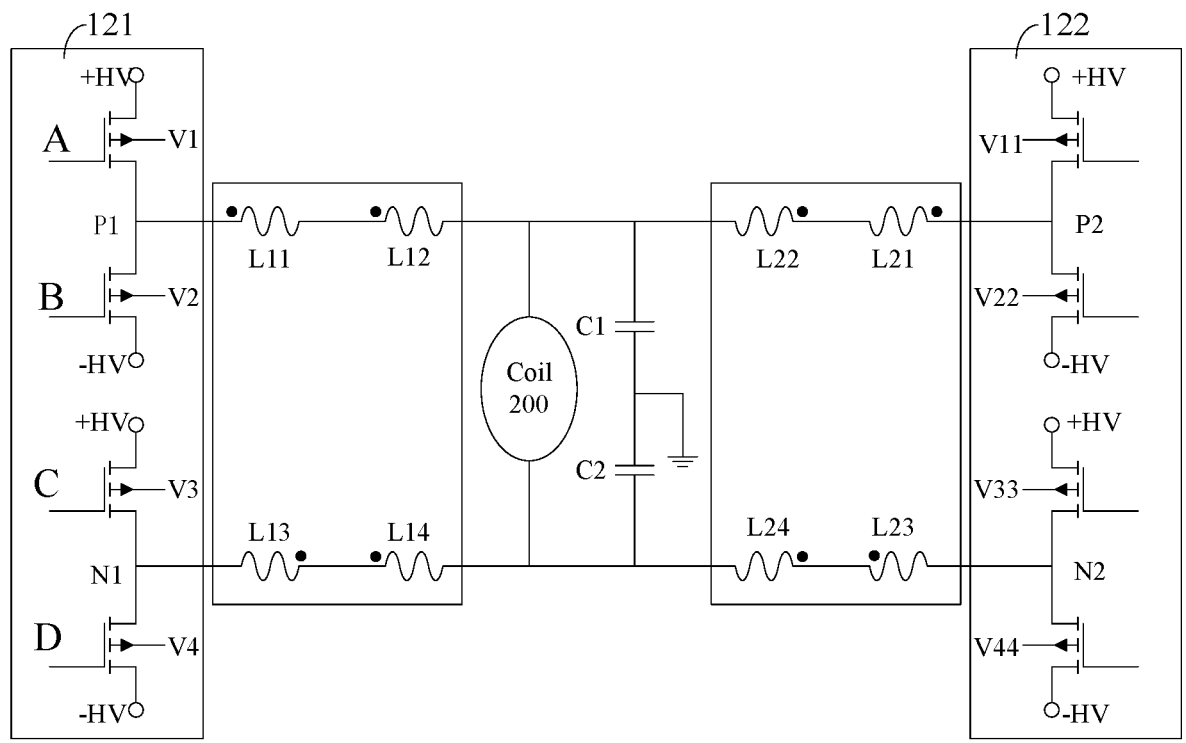
FIG. 3 illustrates an equivalent deformation diagram of a power amplifying circuit and a filtering circuit in FIG. 2.

FIGS. 2 and 3 show a specific topology of the gradient amplifier 100, where FIG. 3 illustrates an equivalent deformation diagram of the power amplifying circuit 120 and the filtering circuit 130 in FIG. 2.

The gradient amplifier 100 provided by the present disclosure is described below in detail according to FIG. 3.

As an example, each of the switching tubes in the two H bridge circuits 121 and 122 is a Negative Metal Oxide Semiconductor (NMOS) tube. It should be understood that each of the switching tubes can be any other suitable tube such as a Metal Oxide Semiconductor Field Effect Transistor (MOSFET) tube or an Insulated Gate Bipolar Transistor (IGBT) tube, which is not limited by the present disclosure.

Since the first H bridge circuit 121 and the second H bridge circuit 122 have the same structure, the following will only describe the first H bridge circuit 121 as an example.

The first H bridge circuit 121 can include two bridge arms, e.g., a first bridge arm and a second bridge arm. The first bridge arm includes a first switching tube V1 and a second switching tube V2. The second bridge arm includes a third switching tube V3 and a fourth switching tube V4. According to a principle that two switching tubes on the same bridge arm cannot be turned on at the same time, the phase of a pulse signal A for driving the first switching tube V1 is opposite to that of a pulse signal B for driving the second switching tube V2. For example, when the first switching tube V1 is turned on, the second switching tube V2 is turned off. The phase of a pulse signal C for driving the third switching tube V3 is opposite to that of a pulse signal D for driving the fourth switching tube V4. For example, when the third switching tube V3 is turned on, the fourth switching tube V4 is turned off. Moreover, the phase difference between the pulse signal A and the pulse signal D is 180 degrees.

Here, the phase of the pulse signal A opposite to that of the pulse signal B means that when the pulse signal A is at a high level, the pulse signal B is at a low level; and when the pulse signal A is at a low level, the pulse signal B is at a high level.

As shown in FIG. 3, P1 is a first output terminal of the first H bridge circuit 121, and N1 is a second output terminal of the first H bridge circuit 121.

In some cases, when the first switching tube V1 and the fourth switching tube V4 are turned on, and the second switching tube V2 and the third switching tube V3 are turned off, a direction of the driving current output by the first H bridge circuit 121 is defined as a positive direction. On the contrary, when the first switching tube V1 and the fourth switching tube V4 are turned off, and the second switching tube V2 and the third switching tube V3 are turned on, the direction of the driving current output by the first H bridge circuit 121 is defined as a negative direction. It may be understood that the positive direction and the negative direction belong to a relative concept, and therefore the two directions may be set reversely.

The differential-mode inductor set of the filter circuit 130 can include a first differential-mode inductor set and a second differential-mode inductor set. The common-mode inductor set of the filter circuit 130 can include a first common-mode inductor set and a second common-mode inductor set.

The first H bridge circuit 121 may be coupled with the first differential-mode inductor set and the first common-mode inductor set. The second H bridge circuit 122 may be coupled with the second differential-mode inductor set and the second common-mode inductor set.

In some examples, the first differential-mode inductor set includes a first differential-mode inductor L11 and a second differential-mode inductor L13. In some cases, the first common-mode inductor set includes a first common-mode inductor L12 and a second common-mode inductor L14. The first differential-mode inductor L11 can be coupled with the second differential-mode inductor L13. The first common-mode inductor L12 can be coupled with the second common-mode inductor L14.

It may be seen from FIG. 3 that the first output terminal P1 of the first H bridge circuit 121 is coupled with the second output terminal N1 of the first H bridge circuit 121 sequentially through the first differential-mode inductor L11, the first common-mode inductor L12, the coil 200, the second common-mode inductor L14 and the second differential-mode inductor L13.

In an example, a dotted terminal (shown by a black dot in FIG. 3) of the first differential-mode inductor L11 is coupled with the first output terminal P1 of the first H bridge circuit 121. A non-dotted terminal of the first differential-mode inductor L11 is coupled with a dotted terminal of the first common-mode inductor L12. A non-dotted terminal of the first common-mode inductor L12 is coupled with a non-dotted terminal of the second common-mode inductor L14 through the coil 200. A dotted terminal of the second common-mode inductor L14 is coupled with a dotted terminal of the second differential-mode inductor L13. A non-dotted terminal of the second differential-mode inductor L13 is coupled with the second output terminal N1 of the first H bridge circuit 121.

The second differential-mode inductor set may include the third differential-mode inductor L21 and the fourth differential-mode inductor L23. The second common-mode inductor set may include the third common-mode inductor L22 and the fourth common-mode inductor L24.

The third differential-mode inductor L21 may be coupled with the fourth differential-mode inductor L23. The third common-mode inductor L22 may be coupled with the fourth common-mode inductor L24.

The connection relationship between the second differential-mode inductor set and the second common-mode inductor set is the same as that between the first differential-mode inductor set and the first common-mode inductor set, and further description is omitted for brevity. It may be seen from FIG. 3 that a first output terminal P2 of the second H bridge circuit 122 is coupled with a second output terminal N2 of the second H bridge circuit 122 sequentially through the third differential-mode inductor L21, the third common-mode inductor L22, the coil 200, the fourth common-mode inductor L24 and the fourth differential-mode inductor L23.

The first H bridge circuit 121 and the second H bridge circuit 122 can share a filtering capacitor. As illustrated in FIG. 3, the filtering capacitor can include a first filtering capacitor C1 and a second filtering capacitor C2. The first filtering capacitor C1 and the second filtering capacitor C2 may be coupled in series between two ends of the coil 200. A common terminal of the first filtering capacitor C1 and the second filtering capacitor C2 may be grounded.

Figure 4:
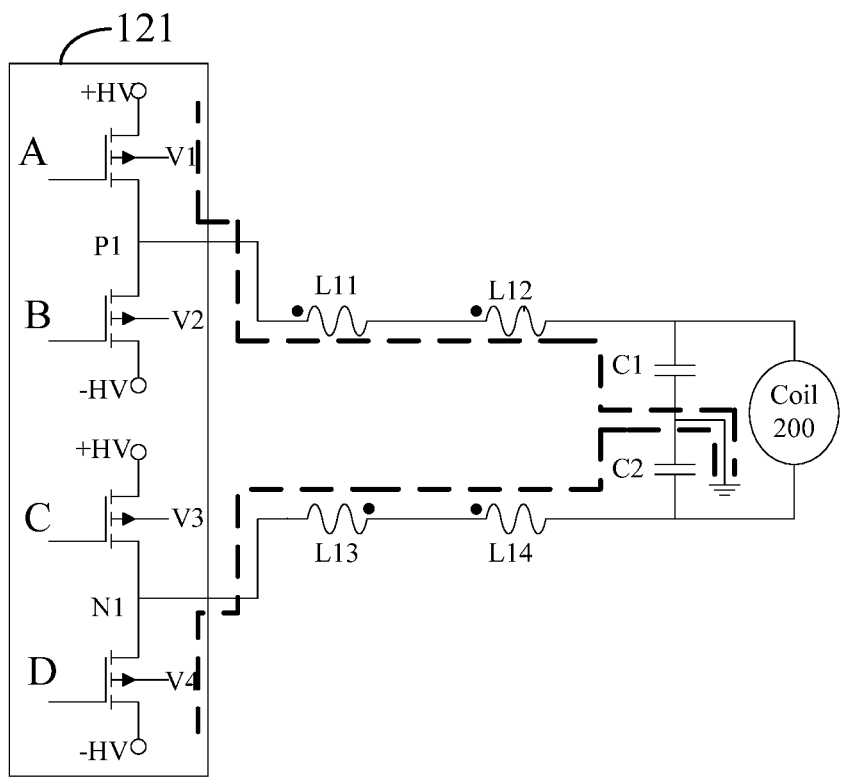
FIG. 4 illustrates a schematic diagram of a path of common-mode noise according to an example of the present disclosure.
Figure 5:
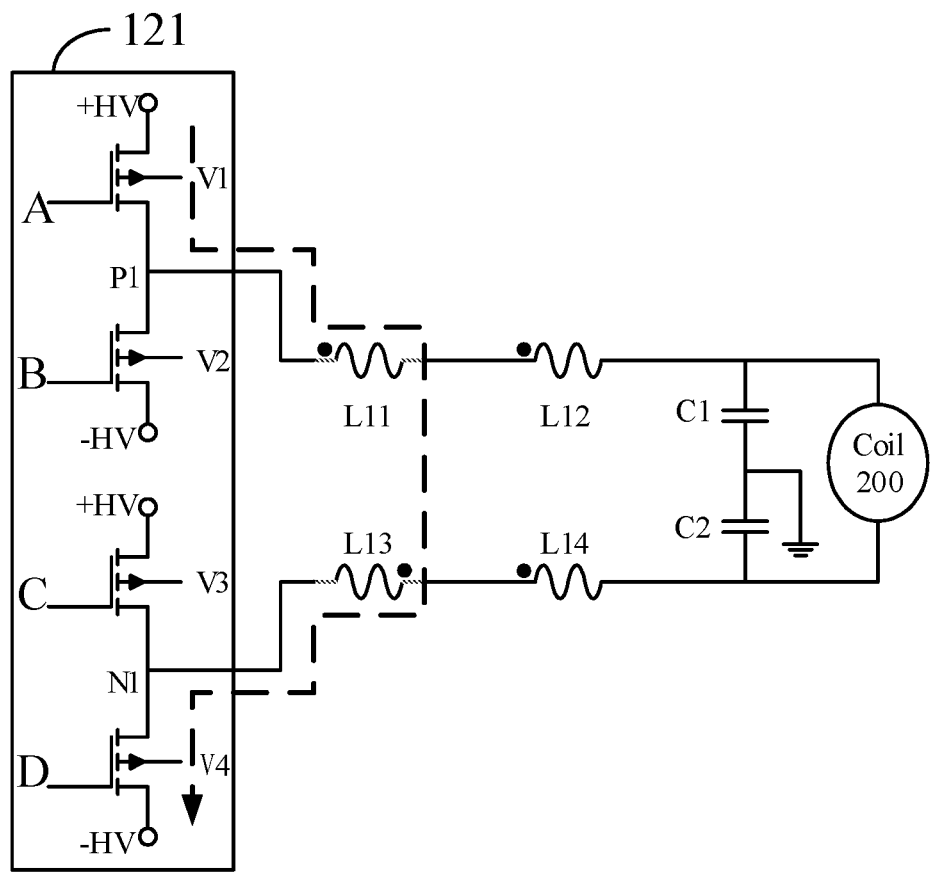
FIG. 5 illustrates a schematic diagram of a path of differential-mode noise according to an example of the present disclosure.

The working principle of the filtering circuit 130 is described in combination with FIGS. 4 and 5. FIG. 4 illustrates a path of common-mode noise and FIG. 5 illustrates a path of differential-mode noise. In FIG. 5, as the first differential-mode inductor L11 is coupled with the second differential-mode inductor L13, the differential-mode noise may reach the second differential-mode inductor L13 through the first differential-mode inductor L11.

The filtering circuit 130 can be configured to eliminate a differential-mode high-frequency harmonic noise and a common-mode high-frequency harmonic noise which are generated when the switching tubes in the double H bridge circuits 121 and 122 are turned on or off.

Taking the first H bridge circuit 121 as an example, when the driving current (mixed with the common-mode noise and the differential-mode noise) output by the first output terminal P1 and the second output terminal N1 passes through the filtering circuit 130, common-mode filtering may be performed through the first common-mode inductor L12, the second common-mode inductor L14, the first filtering capacitor C1 and the second filtering capacitor C2 as shown in FIG. 4. In this way, the common-mode noise in the driving current may be filtered out.

At the same time, as shown in FIG. 5, differential-mode filtering may be performed on the driving current output by the first output terminal P1 and the second output terminal N1 of the first H bridge circuit 121 through the first differential-mode inductor L11 and the second differential-mode inductor L13. In this way, the differential-mode noise in the driving current may be filtered out.

Furthermore, by using the LC resonant circuit including the first differential-mode inductor L11, the first common-mode inductor L12, the first common-mode inductor L13, the second common-mode inductor L14, the first filtering capacitor C1 and the second filtering capacitor C2, the coil 200 may generate an effective output with a relatively small ripple current.

Figure 6:
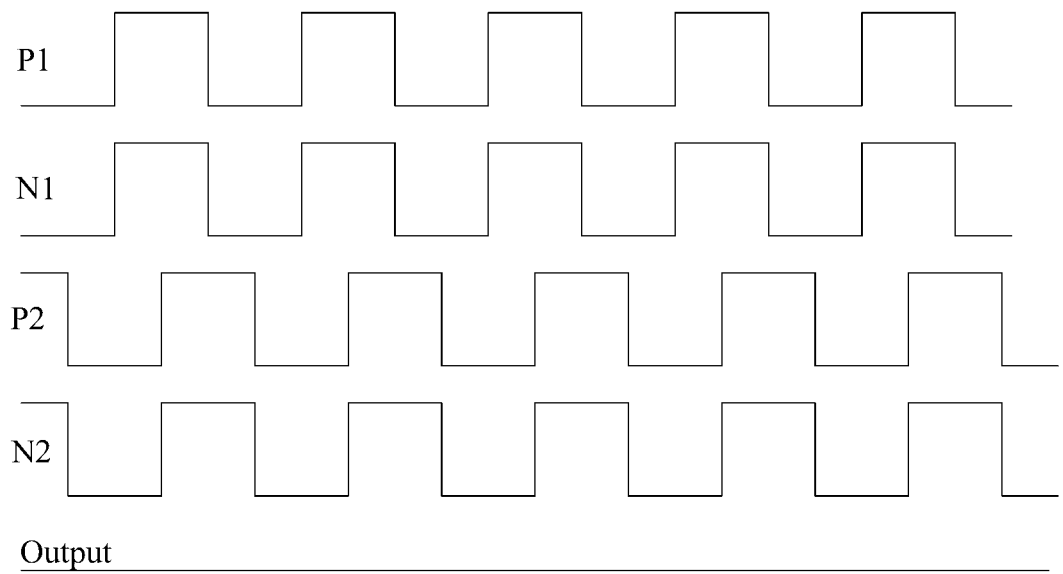
FIG. 6 illustrates a schematic diagram of signal sequences when a duty cycle of each of output signals of a power amplifying circuit is 50% according to an example of the present disclosure.
Figure 7:
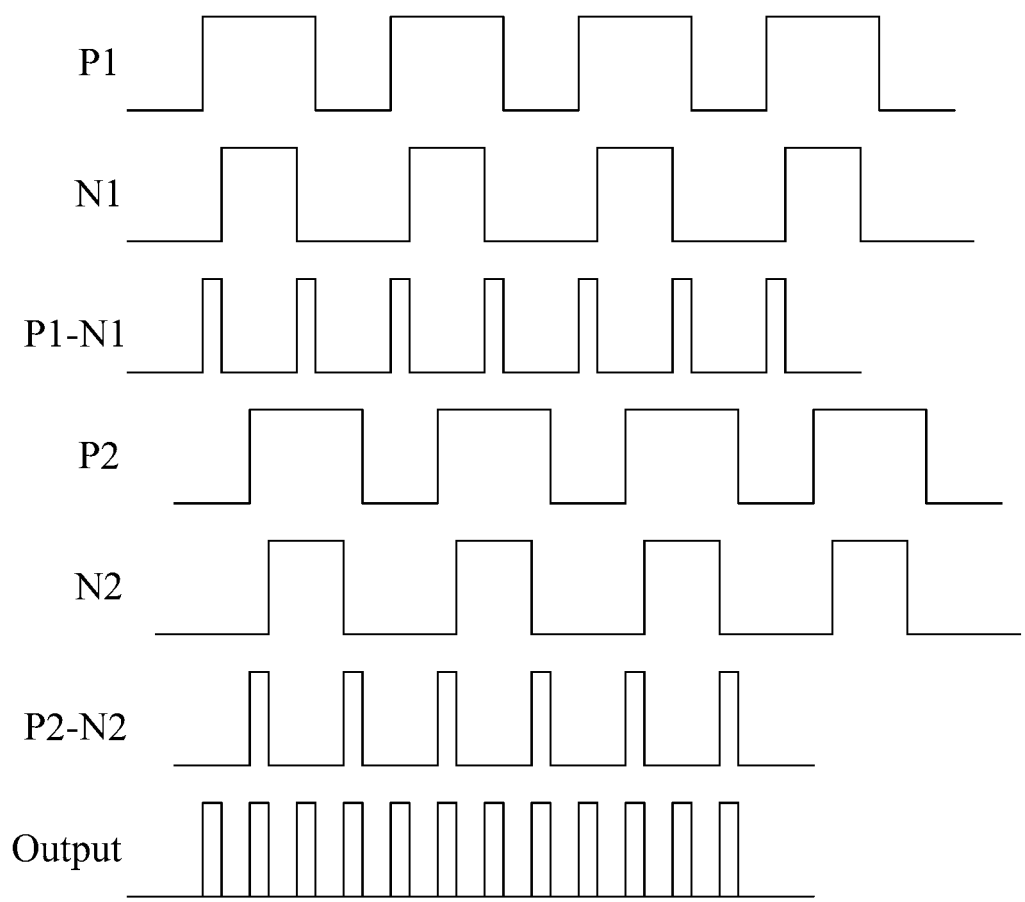
FIG. 7 illustrates a schematic diagram of signal sequences when a duty cycle of each of output signals of a power amplifying circuit is 60% according to an example of the present disclosure.

A working principle of the gradient amplifier 100 is described in combination with FIG. 6 and FIG. 7.

FIG. 6 illustrates a schematic diagram of signal sequences when a duty cycle of each of output signals of double H bridge circuits is 50% according to an example of the present disclosure, where the duty cycle may be a fraction of one period in which a signal or a system is active.

The corresponding duty cycle of each of the first output terminal P1 in the first H bridge circuit, the second output terminal N1 in the first H bridge circuit, the first output terminal P2 in the second H bridge circuit and the second output terminal N2 in the second H bridge circuit is 50%.

It may be seen from FIG. 6 that there is no voltage difference between the output signal of the first output terminal P1 in the first H bridge circuit and the output signal of the second output terminal N1 in the first H bridge circuit. In FIG. 6, the voltage difference between the output signal of the first output terminal P1 in the first H bridge circuit and the output signal of the second output terminal N1 in the first H bridge circuit is zero. Similarly, there is no voltage difference between the output signal of the first output terminal P2 in the second H bridge circuit and the output signal of the second output terminal N2 in the second H bridge circuit. Therefore, there is no effective output formed on the coil 200.

The following will describe a case in which an effective output is formed on the coil 200 combined with FIG. 7.

FIG. 7 illustrates a schematic diagram of signal sequences when a duty cycle of an output signal of double H bridge circuits is 60% according to an example of the present disclosure.

When the corresponding duty cycle of each of the first output terminal P1 in the first H bridge circuit, the second output terminal N1 in the first H bridge circuit, the first output terminal P2 in the second H bridge circuit and the second output terminal N2 in the second H bridge circuit is 60%, it may be seen from FIG. 7 that an output signal shown by P1-N1 is obtained in a way that the output signal of the first output terminal P1 subtracts the output signal of the second output terminal N1, and an output signal shown by P2-N2 is obtained in a way that the output signal of the first output terminal P2 subtracts the output signal of the second output terminal N2.

A final effective output formed on the coil 200 is (P1−N1)+(P2−N2), which is shown by Output in FIG. 7.

It should be noted that the above description is made only with duty cycles 50% and 60% as an example. It should be understood that other value may be selected for the duty cycle. The value of the duty cycle is not limited in the present disclosure and may be selected according to actual requirement, e.g., the value of the duty cycle is flexible.

Based on the gradient amplifier provided by the above embodiments, the present disclosure further provides a method of controlling a gradient amplifier. The method can be performed by a controller, e.g., the controller 110 of FIG. 1. The method can include the following steps: outputting a first group of pulse signals to control turn-on and turn-off of switching tubes of a first H bridge circuit, and outputting a second group of pulse signals to control turn-on and turn-off of switching tubes of a second H bridge circuit, where a phase difference between pulse signals for driving switching tubes on the same position in the first H bridge circuit and the second H bridge circuit is 90 degrees.

In an example, as shown in FIG. 3, the first switching tube V1 in the first H bridge circuit 121 and a first switching tube V11 in the second H bridge circuit 122 are located on the same position. The second switching tube V2 in the first H bridge circuit 121 and a second switching tube V22 in the second H bridge circuit 122 are located on the same position. The third switching tube V3 in the first H bridge circuit 121 and a third switching tube V33 in the second H bridge circuit 122 are located on the same position. The fourth switching tube V4 in the first H bridge circuit 121 and a fourth switching tube V44 in the second H bridge circuit 122 are also located on the same position.

The present disclosure also provides an MRI device which includes a gradient amplifier and a coil, where the gradient amplifier is configured to provide a driving current for the coil; and the coil is configured to generate a magnetic field for the MRI device. The gradient amplifier and the coil can be the gradient amplifier 100 and the coil 200 of FIGS. 1-4.

It should be noted that the coil may be a transmitting coil or a receiving coil. There may be a plurality of coils, for example, a head coil, a shoulder coil and the like. Different regions of a subject may correspond to different coils. For example, when an image of the head of the subject is taken, the head coil may be controlled to work.

In the present disclosure, interference signal (e.g., noise) in the output current for the coil may be filtered out by the filtering circuit. In this way, the driving current for the coil may be relatively accurate and therefore the imaging effect or quality of the MRI device may be guaranteed. In the present disclosure, a phase difference between pulse signals for driving switching tubes on the same position in two H bridge circuits can be 90 degrees, such that the frequency of the driving current for the coil can be doubled compared to the driving current from one of the two H bridge circuits and a high-frequency current signal can be provided for the coil.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. A gradient amplifier comprising:
a controller configured to output pulse signals;
a power amplifying circuit configured to perform power conversion on an input power supply according to the pulse signals to output a driving current, the power amplifying circuit comprising:
  a first H bridge circuit having switching tubes; and
  a second H bridge circuit coupled in parallel with the first H bridge circuit and having an essentially identical structure as the first H bridge circuit,
  wherein a phase difference between the pulse signals output by the controller to drive switching tubes on a same position in the first H bridge circuit and the second H bridge circuit is 90 degrees; and
a filtering circuit configured to filter the driving current output by the power amplifying circuit, the filtering circuit comprising:
  a differential-mode inductor set configured to filter out differential-mode noise in the driving current, and
  a common-mode inductor set configured to filter out common-mode noise in the driving current,
wherein the differential-mode inductor set comprises a first differential-mode inductor set including a first differential-mode inductor and a second differential-mode inductor, the first differential-mode inductor being coupled with the second differential-mode inductor, and wherein the common-mode inductor set comprises a first common-mode inductor set including a first common-mode inductor and a second common-mode inductor, the first common-mode inductor being coupled with the second common-mode inductor,
wherein a first output terminal of the first H bridge circuit is coupled with a second output terminal of the first H bridge circuit sequentially through the first differential-mode inductor, the first common-mode inductor, two output terminals of the filtering circuit, the second common-mode inductor and the second differential-mode inductor,
wherein a first terminal of the first differential-mode inductor is coupled with the first output terminal of the first H bridge circuit, wherein a second terminal of the first differential-mode inductor is coupled with a first terminal of the first common-mode inductor, wherein a second terminal of the first common-mode inductor is coupled with a second terminal of the second common-mode inductor, wherein a first terminal of the second common-mode inductor is coupled with a first terminal of the second differential-mode inductor, and wherein a second terminal of the second differential-mode inductor is coupled with the second output terminal of the first H bridge circuit,
wherein the differential-mode inductor set comprises a second differential-mode inductor set including a third differential-mode inductor and a fourth differential-mode inductor, the third differential-mode inductor being coupled with the fourth differential-mode inductor, and wherein the common-mode inductor set comprises a second common-mode inductor set including a third common-mode inductor and a fourth common-mode inductor, the third common-mode inductor being coupled with the fourth common-mode inductor,
wherein a first output terminal of the second H bridge circuit is coupled with a second output terminal of the second H bridge circuit sequentially through the third differential-mode inductor, the third common-mode inductor, the two output terminals of the filtering circuit, the fourth common-mode inductor and the fourth differential-mode inductor, and
wherein a first terminal of the third differential-mode inductor is coupled with the first output terminal of the second H bridge circuit, wherein a second terminal of the third differential-mode inductor is coupled with a first terminal of the third common-mode inductor, wherein a second terminal of the third common-mode inductor is coupled with a second terminal of the fourth common-mode inductor, wherein a first terminal of the fourth common-mode inductor is coupled with a first terminal of the fourth differential-mode inductor, and wherein a second terminal of the fourth differential-mode inductor is coupled with the second output terminal of the second H bridge circuit.

2. The gradient amplifier according to claim 1, further comprising a filtering capacitor,
wherein the filtering capacitor comprises:
  a first filtering capacitor; and
  a second filtering capacitor,
  wherein the second filtering capacitor and the first filtering capacitor are coupled in series between the first and second output terminals of the filtering circuit, and
  wherein a common terminal of the first filtering capacitor and the second filtering capacitor is grounded.

3. The gradient amplifier according to claim 1, wherein the first H bridge circuit comprises a first switching tube, a second switching tube, a third switching tube and a fourth switching tube, wherein the first switching tube and the second switching tube are coupled in series between a positive and a negative of the input power supply, and a common terminal of the first switching tube and the second switching tube serves as the first output terminal of the first H bridge circuit, wherein the third switching tube and the fourth switching tube are coupled in series between the positive and the negative of the input power supply, and a common terminal of the third switching tube and the fourth switching tube serves as the second output terminal of the first H bridge circuit, and wherein the pulse signals for driving the first switching tube and the second switching tube are of opposite phases, the pulse signals for driving the third switching tube and the fourth switching tube are of opposite phases, and a phase difference between the pulse signals for driving the first switching tube and the fourth switching tube is 180 degrees.

4. The gradient amplifier according to claim 1, wherein the switching tubes in the first H bridge circuit and the second H bridge circuit include at least one of a Negative Metal Oxide Semiconductor (NMOS) tube, an Insulated Gate Bipolar Transistor (IGBT) tube, or a Metal Oxide Semiconductor Field Effect Transistor (MOSFET) tube.

5. A magnetic resonance imaging (MM) device, comprising:
a coil configured to generate a magnetic field; and
a gradient amplifier configured to provide a driving current for the coil and comprising:
a controller configured to output pulse signals;
a power amplifying circuit configured to perform power conversion on an input power supply according to the pulse signals to output the driving current, the power amplifying circuit comprising:
a first H bridge circuit including switching tubes; and
a second H bridge circuit coupled in parallel with the first H bridge circuit and having an essentially identical structure as the first H bridge circuit,
wherein a phase difference between the pulse signals output by the controller to drive the switching tubes on a same position in the first H bridge circuit and the second H bridge circuit is 90 degrees; and
a filtering circuit configured to filter the driving current output by the power amplifying circuit and comprising:
a differential-mode inductor set configured to filter out differential-mode noise in the driving current; and
a common-mode inductor set configured to filter out common-mode noise in the driving current,
wherein the differential-mode inductor set comprises a first differential-mode inductor set including a first differential-mode inductor and a second differential-mode inductor, the first differential-mode inductor being coupled with the second differential-mode inductor, and wherein the common-mode inductor set comprises a first common-mode inductor set including a first common-mode inductor and a second common-mode inductor, the first common-mode inductor being coupled with the second common-mode inductor,
wherein a first output terminal of the first H bridge circuit is coupled with a second output terminal of the first H bridge circuit sequentially through the first differential-mode inductor, the first common-mode inductor, two output terminals of the filtering circuit, the second common-mode inductor and the second differential-mode inductor,
wherein a first terminal of the first differential-mode inductor is coupled with the first output terminal of the first H bridge circuit, wherein a second terminal of the first differential-mode inductor is coupled with a first terminal of the first common-mode inductor, wherein a second terminal of the first common-mode inductor is coupled with a second terminal of the second common-mode inductor, wherein a first terminal of the second common-mode inductor is coupled with a first terminal of the second differential-mode inductor, and wherein a second terminal of the second differential-mode inductor is coupled with the second output terminal of the first H bridge circuit,
wherein the differential-mode inductor set comprises a second differential-mode inductor set including a third differential-mode inductor and a fourth differential-mode inductor, the third differential-mode inductor being coupled with the fourth differential-mode inductor, and wherein the common-mode inductor set comprises a second common-mode inductor set including a third common-mode inductor and a fourth common-mode inductor, the third common-mode inductor being coupled with the fourth common-mode inductor,
wherein a first output terminal of the second H bridge circuit is coupled with a second output terminal of the second H bridge circuit sequentially through the third differential-mode inductor, the third common-mode inductor, the two output terminals of the filtering circuit, the fourth common-mode inductor and the fourth differential-mode inductor, and
wherein a first terminal of the third differential-mode inductor is coupled with the first output terminal of the second H bridge circuit, wherein a second terminal of the third differential-mode inductor is coupled with a first terminal of the third common-mode inductor, wherein a second terminal of the third common-mode inductor is coupled with a second terminal of the fourth common-mode inductor, wherein a first terminal of the fourth common-mode inductor is coupled with a first terminal of the fourth differential-mode inductor, and wherein a second terminal of the fourth differential-mode inductor is coupled with the second output terminal of the second H bridge circuit.

6. The device according to claim 5, further comprising a filtering capacitor,
wherein the filtering capacitor comprises:
a first filtering capacitor; and
a second filtering capacitor,
wherein the second filtering capacitor and the first filtering capacitor are coupled in series between the first and second output terminals of the filtering circuit, and
wherein a common terminal of the first filtering capacitor and the second filtering capacitor is grounded.

7. The device according to claim 5, wherein the first H bridge circuit comprises a first switching tube, a second switching tube, a third switching tube and a fourth switching tube,
wherein the first switching tube and the second switching tube are coupled in series between an positive and a negative of the input power supply, and a common terminal of the first switching tube and the second switching tube serves as the first output terminal of the first H bridge circuit, wherein the third switching tube and the fourth switching tube are coupled in series between the positive and the negative of the input power supply, and a common terminal of the third switching tube and the fourth switching tube serves as the second output terminal of the first H bridge circuit, and wherein the pulse signals for driving the first switching tube and the second switching tube are of opposite phases, the pulse signals for driving the third switching tube and the fourth switching tube are of opposite phases, and a phase difference between the pulse signals for driving the first switching tube and the fourth switching tube is 180 degrees.

8. The device according to claim 5, wherein the switching tubes of the first H bridge circuit and the second bridge circuit comprise at least one of a Negative Metal Oxide Semiconductor (NMOS) tube, an Insulated Gate Bipolar Transistor (IGBT) tube, or a Metal Oxide Semiconductor Field Effect Transistor (MOSFET) tube.

9. A method comprising:
outputting, by a controller of a gradient amplifier, a first group of pulse signals to respectively control each of switching tubes in a first H bridge circuit of a power amplifying circuit of the gradient amplifier;
outputting, by the controller, a second group of pulse signals to respectively control each of switching tubes in a second H bridge circuit of the power amplifying circuit, wherein the first H bridge circuit and the second H bridge circuit have an essentially identical structure and are coupled in parallel to form the power amplifying circuit, and wherein the pulse signals for driving the switching tubes on a same position in the first H bridge circuit and the second H bridge circuit have a particular phase difference;
performing, by the power amplifying circuit, power conversion on an input power supply according to the pulse signals to output a driving current; and
filtering, by a filtering circuit of the gradient amplifier, the driving current output by the power amplifying circuit, wherein the filtering circuit comprises:
a differential-mode inductor set configured to filter out differential-mode noise in the driving current, and
a common-mode inductor set configured to filter out common-mode noise in the driving current,
wherein the differential-mode inductor set comprises a first differential-mode inductor set including a first differential-mode inductor and a second differential-mode inductor, the first differential-mode inductor being coupled with the second differential-mode inductor, and wherein the common-mode inductor set comprises a first common-mode inductor set including a first common-mode inductor and a second common-mode inductor, the first common-mode inductor being coupled with the second common-mode inductor,
wherein a first output terminal of the first H bridge circuit is coupled with a second output terminal of the first H bridge circuit sequentially through the first differential-mode inductor, the first common-mode inductor, two output terminals of the filtering circuit, the second common-mode inductor and the second differential-mode inductor,
wherein a first terminal of the first differential-mode inductor is coupled with the first output terminal of the first H bridge circuit, wherein a second terminal of the first differential-mode inductor is coupled with a first terminal of the first common-mode inductor, wherein a second terminal of the first common-mode inductor is coupled with a second terminal of the second common-mode inductor, wherein a first terminal of the second common-mode inductor is coupled with a first terminal of the second differential-mode inductor, and wherein a second terminal of the second differential-mode inductor is coupled with the second output terminal of the first H bridge circuit, wherein the differential-mode inductor set comprises a second differential-mode inductor set including a third differential-mode inductor and a fourth differential-mode inductor, the third differential-mode inductor being coupled with the fourth differential-mode inductor, and wherein the common-mode inductor set comprises a second common-mode inductor set including a third common-mode inductor and a fourth common-mode inductor, the third common-mode inductor being coupled with the fourth common-mode inductor, wherein a third output terminal of the second H bridge circuit is coupled with a fourth output terminal of the second H bridge circuit sequentially through the third differential-mode inductor, the third common-mode inductor, the two output terminals of the filtering circuit, the fourth common-mode inductor and the fourth differential-mode inductor, and wherein a first terminal of the third differential-mode inductor is coupled with the third output terminal of the second H bridge circuit, wherein a second terminal of the third differential-mode inductor is coupled with a first terminal of the third common-mode inductor, wherein a second terminal of the third common-mode inductor is coupled with a second terminal of the fourth common-mode inductor, wherein a first terminal of the fourth common-mode inductor is coupled with a first terminal of the fourth differential-mode inductor, and wherein a second terminal of the fourth differential-mode inductor is coupled with the fourth output terminal of the second H bridge circuit.

10. The method according to claim 9, wherein the first H bridge circuit comprises the first and second output terminals coupled to two respective ends of a coil and is configured to output first and second output signals at the first and second output terminals, respectively,
wherein outputting a first group of pulse signals comprises outputting the first group of pulses signals to control the first and second output signals to form a first driving current flowing through the coil,
wherein the second H bridge circuit comprises the third and fourth output terminals coupled to the two respective ends of the coil and is configured to output third and fourth output signals at the third and fourth output terminals, respectively, and
wherein outputting a second group of pulse signals comprises outputting the second group of pulses signals to control the third and fourth output signals to form a second driving current flowing through the coil.

11. The method according to claim 10, wherein the particular phase difference is configured such that a total driving current on the coil that is based on the first driving current and the second driving current has a higher frequency than one of the first driving current and the second driving current.

12. The method according to claim 11, wherein the particular phase difference is 90 degrees, and a frequency of the total driving current is doubled compared to a frequency of the one of the first driving current and the second driving current.

\* \* \* \* \*